US00PP08731P

United States Patent [19]

Bartels

[11] Patent Number: Plant 8,731

[45] Date of Patent: May 17, 1994

[54] ASTER PLANT NAMED PINK MASTER

[75] Inventor: G. B. H. Bartels, Hornweg 53, 1432 GD Aalsmeer, Netherlands

[73] Assignee: G. B. H. Bartels, Aalsmeer, Netherlands

[21] Appl. No.: 86,146

[22] Filed: Jul. 6, 1993

[51] Int. Cl.[5] ..... A01H 5/00

[52] U.S. Cl. ..... Plt./68.1

[58] Field of Search ..... Plt. 68.1

*Primary Examiner*—James R. Feyrer

*Attorney, Agent, or Firm*—G. B. H. Bartels

[57] ABSTRACT

A distinct cultivar of aster plant named Pink Master, characterized by its large inflorescences, large number of ray and disc florets, non-fading inflorescence color, large number of harvestable stems per plant, strong and straight stems, and good postharvest keeping quality.

1 Drawing Sheet

The present invention relates to a new and distinctive cultivar of Aster hybrid, hereinafter referred to by the cultivar name Pink Master.

The new cultivar was developed by me at Bartelstek, Aalsmeer, Holland, through controlled breeding by crossing the cultivar identified as 89-288 pink as the female parent with the cultivar identified as 89-274 pink as the male parent. Both parents are hybrids of aster cultivars, species unknown.

Asexual reproduction of the new cultivar by terminal or stem cuttings taken at Aalsmeer, Holland, has shown that the unique features of this new aster are stabilized and are reproduced true to type in successive generations of asexual reproduction.

The following characteristics distinguish the new aster from both its parent varieties and other cultivated asters of this type known and used in the floriculture industry:

1. Pink Master has large inflorescences which are distinctive.
2. Pink Master has more ray florets per inflorescence than comparable cultivars.
3. Ray florets of Pink Master do not fade with maturity.
4. Pink Master plants produced more flowering stems than comparable cultivars.
5. Flowering stems of Pink Master are stronger and straighter than comparable cultivars.
6. Cut flowering stems of Pink Master consistently demonstrate good postharvest longevity.

The accompanying colored photographs illustrate the overall appearance and flower color of the new cultivar, showing the colors as true as it is reasonably possible to obtain in colored reproductions of this type. The photograph is a single flowering stem of Pink Master.

The new cultivar can be compared in certain characteristics to the nonpatented cultivar Pink Star. In general comparison to Pink Star, Pink Master has:

1. Larger inflorescences, two times larger in diameter than Pink Star.
2. More ray and disc florets, on average 1.75 times more ray and disc florets giving fuller inflorescence form.
3. Ray floret color does not fade compared to Pink Star.
4. More harvestable stems per plant, on average 20 percent more stems than Pink Star.

5. Stronger and straighter stems than Pink Star.
6. Postharvest keeping quality is 20 percent longer than Pink Star.

The following is a detailed description of my new cultivar based on plants produced under normal commercial practice in Aalsmeer, Holland in a glass-covered greenhouse with day temperature of 16° to 18° C. and night temperature of 12° C. during the vegetative phase and day temperatures of 22° to 25° C. and night temperatures of 18° C. during the flowering phase.

Color references are made to The Royal Horticultural Society Colour Chart except where general terms of ordinary dictionary significance are used.

Botanical classification: Aster hybrid cv Pink Master.

Parentage:

*Male parent.*—Bartelstek 89-274 pink.

*Female parent.*—Bartelstek 89-288 pink.

Propagation:

A. *Type.*—By terminal tip cuttings, tissue culture and division.

B. *Time to initiate roots.*—14 days at 25° C. during the summer.

C. *Time to initiate roots.*—20 days at 20 C. during the winter.

D. *Rooting habit.*—Fibrous, branching.

Plant description:

A. *General appearance.*—Upright, freely branching and vigorous.

B. *Foliage description.*—Shape: Linear, elongated, narrow. Size: 6.5 cm in length, 0.3 cm in width. Texture: Smooth, not pubescent. Margin: Entire. Color: Young foliage top side: 147A. Young foliage under side: 147A. Mature foliage top side: 147A. Mature foliage under side: 147A. Venation: Parallel, branched, color is 147A.

Flowering description:

A. *Flowering habit.*—Panicles of florets, radiate capitula.

B. *Natural flowering season.*—Natural flowering season is the fall in the northern hemisphere.

C. *Quantity of flowers.*—More than ten inflorescences on each lower flowering lateral stem and more than 150 inflorescences per each harvested stem.

D. Ray florets.—Shape: Ligulate. Color: Top side: 77D. When opening: 77B. Fading to: 77D. Under side: 77D. Number of ray florets: Double rows, more than 50 ray florets per inflorescence. Size of inflorescence: 3.25 cm in diameter.

E. *Disc florets.*—Shape: Tubular. Color: Color mature: 6A. Color immature: 6B. Number of disc florets: More than 50 per inflorescence. Diameter of disc: 1 cm.

F. *Reproductive organs.*—Stamens: Anther color: 2A. Pollen color: 2A. Pistils: Stigma color: 6C. Style color: 144C.

Disease resistance: No fungal or bacterial problems observed to date.

I claim:

1. A new and distinct cultivar of aster plant named Pink Master, as illustrated and described.

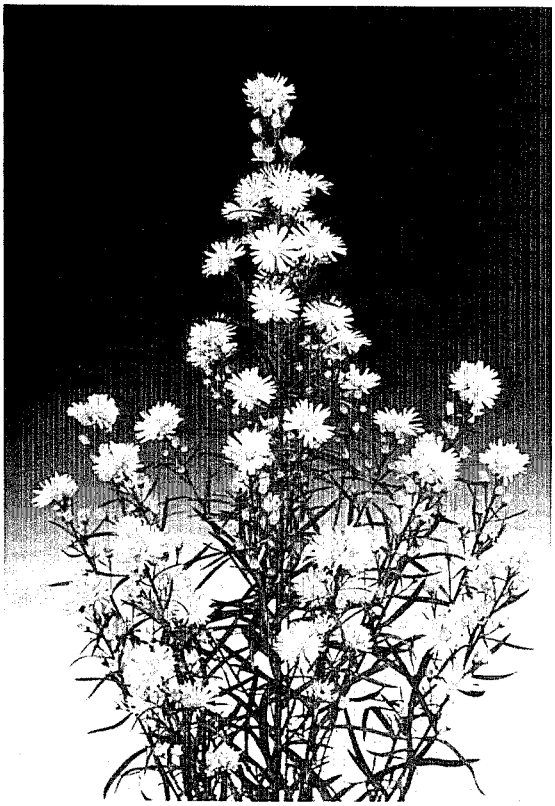

* * * * *